United States Patent [19]

Jung

[11] Patent Number: 4,780,445

[45] Date of Patent: Oct. 25, 1988

[54] SELECTIVE CATALYTIC REDUCTION CATALYST CONSISTING ESSENTIALLY OF NICKEL AND/OR MANGANESE SULFATE, CERIA AND ALUMINA

[75] Inventor: Hyun J. Jung, Wayne, Pa.

[73] Assignee: Johnson Matthey Inc., Malvern, Pa.

[21] Appl. No.: 69,705

[22] Filed: Jun. 30, 1987

Related U.S. Application Data

[62] Division of Ser. No. 874,154, Jun. 13, 1984, Pat. No. 4,695,457.

[51] Int. Cl.[4] ................ B01J 27/053; B01J 21/04
[52] U.S. Cl. ................................. 502/217; 502/304
[58] Field of Search ................ 502/217, 218, 304

[56] References Cited

U.S. PATENT DOCUMENTS

| | | | |
|---|---|---|---|
| 4,107,272 | 8/1978 | Mori et al. | 502/218 |
| 4,115,516 | 9/1978 | Takami et al. | 423/239 A |
| 4,331,565 | 5/1982 | Schefer et al. | 502/304 |

FOREIGN PATENT DOCUMENTS 2554515  5/1975  Fed. Rep. of Germany ...... 502/218

*Primary Examiner*—Paul E. Konopka
*Attorney, Agent, or Firm*—Cushman, Darby & Cushman

[57] ABSTRACT

An SCR catalyst consisting essentially of at least one oxysulfur compound of manganese, nickel or mixtures thereof, carried by a supported mixture of ceria and alumina. The catalyst is characterized by its high activity and by its stability even when used in the absence of sulfur oxides.

3 Claims, No Drawings

SELECTIVE CATALYTIC REDUCTION CATALYST CONSISTING ESSENTIALLY OF NICKEL AND/OR MANGANESE SULFATE, CERIA AND ALUMINA

"This application is a division of U.S. application Ser. No. 874,154, filed June 13, 1986, now U.S. Pat. No. 4,695,437."

The present invention is concerned with improved selective catalytic reduction catalysts. For ease of reference these catalysts are hereinafter referred to as "SCR" catalysts.

BACKGROUND OF THE INVENTION

It is known to remove oxides of nitrogen ($NO_x$) pollutants from exhaust streams or other gaseous emission sources which contain excess oxygen by adding $NH_3$ to the gas stream in a proportion based on the amount of $NO_x$ present and reacting the $NH_3$ and $NO_x$ over a catalyst to form non-polluting $N_2$ and $H_2O$.

A wide variety of catalysts have been proposed for this purpose. See, for example, U.S. Pat. Nos. 3,279,884 and 4,115,516. Vanadium pentoxide or other oxide supported on alumina has been extensively used as an SCR catalyst. Cerium oxide has also been proposed. See, for instance, the abovementioned U.S. Pat. No. 4,115,516 as well as U.S. Pat. No. 3,885,019.

Oxysulfur compounds of manganese, iron and nickel have also been disclosed as active SCR catalysts in U.S. Pat. No. 4,107,272. However, it has been found that manganese and nickel catalysts prepared according to the prior art have low SCR activities and cannot, therefore, be used commercially. Iron sulfate catalysts prepared according to the prior art do provide commercially useful SCR performance over short periods of time but they are not durable and their activity diminishes in use, particularly when they are employed in the processing of flue gases containing only low concentrations of sulfur oxides ($SO_x$).

The principal object of the present invention is to provide SCR catalysts based on the use of one or more oxysulfur compounds of manganese and/or nickel, and optionally iron oxysulfur compounds, which demonstrate a commercially useful SCR activity that is durable over long periods of use whether or not sulfur oxides are present.

GENERAL DESCRIPTION OF THE INVENTION

Broadly stated, the catalyst of the invention consists essentially of at least one metal selected from the group consisting of manganese and nickel in the form of an oxysulfur compound thereof, optionally with an oxysulfur compound of iron, on a supported carrier consisting essentially of a mixture of $CeO_2$ and $Al_2O_3$. The support for the carrier may comprise any of the conventional ceramic or metallic supports.

It is essential to the success of the invention that the indicated sulfates or oxysulfur compounds be carried on a mixture of ceria and alumina rather than alumina or ceria alone. Thus, according to the invention, it has been found that when oxysulfur compounds of manganese and/or nickel are carried on the mixture of ceria and alumina, the resulting catalysts have unexpectedly higher SCR activity than the same oxysulfur compounds have when carried on alumina or ceria alone. The manganese or nickel oxysulfur compounds supported on ceria-alumina according to the invention are also much more active than mixtures of ceria and alumina which do not include the oxysulfur compounds.

It has also been found that oxysulfur compounds of manganese and nickel when supported on ceria-alumina according to the invention, particularly manganese (II) sulfate and nickel (II) sulfate, are thermally much more stable than similarly supported iron (III) sulfate at elevated temperature in the absence of $SO_2$. For example, at an $SO_2$ concentration of 0.01 ppm, manganese (II) sulfate and nickel (II) sulfate do not decompose at temperatures of up to 560° C. and 460° C., respectively while iron (III) sulfate decomposes at around 350° C. Thus, manganese (II) sulfate or nickel (II) sulfate supported on ceria-alumina can provide durable, long life-time SCR catalysts for use at elevated temperatures with flue gases containing low concentrations, (e.g. <200 ppm) of sulfur oxides.

The invention is, therefore, based on the finding that oxysulfur compounds of nickel or manganese or mixtures thereof, optionally along with oxysulfur compounds of iron, supported on a carrier consisting of a mixture of $CeO_2$ and $Al_2O_3$ constitute particularly advantageous SCR catalyst compositions which are commercially more useful than prior art metal sulfate SCR catalyst formulations because of their improved SCR activity and/or life time, even when used to treat flue gases containing a wide range of sulfur oxide concentrations.

DETAILED DESCRIPTION OF THE INVENTION

The amount of ceria, alumina, and oxysulfur compound(s) of manganese and/or nickel included in the present catalysts can be varied. However, the carrier preferably comprises 2–60% by weight of ceria, balance alumina. The amount of oxysulfur compounds of manganese and/or nickel normally should be in the range of 1 to 25% by weight of manganese and/or nickel metal based on the carrier weight. The amount of oxysulfur compound of iron, if used, will usually fall in the range of 0 to 25% by weight of iron based on the weight of the ceria-alumina carrier. It has been found that this amount of iron in the form of oxysulfate does not undesirably affect the thermal stability or durability of the catalyst.

The ceria-alumina carrier may be prepared in a variety of ways. Thus, for example, ceria or ceria precursor (e.g. cerium hydrate) and alumina powder or alumina precursor may be directly mixed together in the desired amounts, advantageously as a slurry in water. This may then be applied to any conventional ceramic or metal support material, e.g. a ceramic honeycomb made from cordierite or the equivalent as commercially available, or high temperature alloy such as the Kanthal or Fecralloy type alloys, steels, etc. in the usual manner, followed by drying and calcining. The oxysulfur compound(s) of manganese and/or nickel, optionally with oxysulfur compound of iron, are thereafter applied, usually in the form of an aqueous solution or slurry followed by drying and calcining.

The catalyst of the invention is used under conventional SCR conditions although, because of the greater activity of the catalyst, less $NH_3$ and/or catalyst may be used to obtain effective $NO_x$ abatement than would be possible using conventional catalysts. Representative SCR conditions, using the present catalyst involve mixing $NH_3$ in the exhaust gas stream containing $NO_x$ at a molar ratio with the $NO_x$ of from 0.4 to 2.0, and contacting the mixture with the catalyst at a temperature of 250° C. to 500° C. at a GHSV of 1000 hr$^{-1}$ to 50,000 hr$^{-1}$. The catalyst is particularly effective for use with gases of the type indicated containing SO$_x$ at concentration levels of up to, for example, 1500 ppm.

In a preferred way of practicing the invention, the catalyst is prepared as follows:

A washcoat slurry is prepared by comingling ceria and gamma-alumina. A ceramic or metallic monolith is washcoated with the mixed ceria-alumina slurry. The washcoated monolith is then dried and calcined at 500° C. for 30 minutes. The washcoated monolith is then impregnated with an aqueous solution of manganese (II) sulfate, nickel (II) sulfate, and iron (III) sulfate in the desired proportions, dried, and calcined at 300° C. to 500° C. In use, the catalyst is installed in a conventional SCR system at a place in the waste gas where the temperature is in the range of 350°–450° C. NH$_3$ is injected into the gas stream upstream of the catalyst. The catalyst achieves NO$_x$ removal in excess of 85% in the temperature range of 350°–450° C. with an NH$_3$/NO$_x$ ratio of 1.0 and gas hour space velocity (GHSV) range of 30,000–35,000 hr$^{-1}$ without decomposition of metal sulfate to metal oxide and without catalyst deactivation even during use with flue gases containing sulfur oxides in the concentration range of 0 and 1500 ppm.

The following examples are representative of the invention. However, it will be understood that these are given for purposes of illustration and are not intended to limit the invention:

EXAMPLE 1

A cordierite honeycomb monolith with 400 cells per square inch was washcoated with 5200 g of gamma-alumina per cubic foot volume of monolith. The washcoated monolith was then dried and calcined at 500° C. for 30 minutes.

Comparative Example Catalyst A was prepared by impregnating the monolith with an aqueous solution of Fe$_2$(SO$_4$)$_3$.H$_2$O at a Fe loading of 340 g per cubic foot volume of monolith, drying the catalyst at 120° C. for 1 hour and further calcining it at 450° C. for 30 minutes.

Comparative Example Catalyst B was prepared by impregnating the alumina-washcoated monolith with an aqueous solution of Ni(SO$_4$).6H$_2$O at a Ni loading of 250 g per cubic foot volume of monolith, in the same manner as above.

Comparative Example Catalyst C was prepared by impregnating the alumina-washcoated monolith with an aqueous solution of Mn(SO$_4$).H$_2$O at Mn loading of 81 g per cubic foot volume of monolith, in the same manner as above.

Comparative Example Catalyst D was prepared by aging Comparative Example Catalyst A for 72 hours at 400° C. in a flow of SO$_x$-free exhaust gas generated from the combustion of propane in excess of oxygen.

A continuous-flow reactor was loaded with a 4.7 cubic inch of monolith catalyst sample. A simulated turbine exhaust gas consisting of 42 ppm NO, 15% O$_2$, 45% CO$_2$, 10% H$_2$O and the balance of N$_2$ was introduced, after being admixed with 42 ppm NH$_3$, into the reactor at a flow rate of 45.05 standard liters per minute (35,000 hr$^{-1}$ GHSV) at a temperature of 300° to 500° C. The discharge gas was measured for NO concentration at the outlet of the reactor to determine relations between the catalyst temperature and the percent NO reduction. The results are given in Table 1.

It is evident from the reactor test results that the alumina-supported iron sulfate catalyst can not be useful commercially because of short life time, and the alumina-supported nickel sulfate and manganese sulfate catalysts can not be useful commercially because of low activity.

EXAMPLE 2

A washcoat was prepared by co-mingling 1500 g ceria and 3000 g gamma-alumina. A cordierite honeycomb monolith with 400 cells per square inch was washcoated with the co-mingled ceria and alumina. The washcoat loading was 4500 g per cubic foot volume of monolith. Comparative Example Catalyst E was prepared by drying and calcining the washcoated monolith at 500° C. for 30 minutes.

Example Catalyst A was prepared by impregnating the ceria-alumina washcoated monolith with an aqueous solution of NiSO$_4$.6H$_2$O at a Ni loading of 250 g per cubic foot volume of monolith, drying the catalyst at 120° C. for 1 hour and further calcining it at 450° C. for 30 minutes.

Example Catalyst B was prepared by aging Example Catalyst A for 256 hours at 400° C. in a flow of wet (10 volume % H$_2$O) air which was free of SO$_x$.

Example Catalyst C was prepared by impregnating the ceria-alumina washcoated monolith with an aqueous solution of MnSO$_4$.H$_2$O at a Mn loading of 80 g per cubic foot volume of monolith, in the same manner as Example Catalyst A.

Example Catalyst D was prepared by impregnating the ceria-alumina washcoated monolith with an aqueous solution of MmSO$_4$.H$_2$O at a Mn loading of 160 g per cubic foot volume of monolith, in the same manner as Example Catalyst A.

Example Catalyst E was prepared by aging Example Catalyst D for 256 hours at 400° C. in the same manner as Example Catalyst B.

Example Catalyst F was prepared by impregnating the ceria-alumina washcoated monolith with an aqueous solution of Mn(SO$_4$).H$_2$O and Fe$_2$(SO$_4$)$_3$.H$_2$O at a Mn loading of 80 g per cubic foot volume of monolith and an Fe loading of 28 g per cubic foot volume of monolith, in the same manner as Example Catalyst A.

EXAMPLE 3

A washcoat was prepared by co-mingling 1500 g ceria and 3000 g gamma-alumina. A metallic SR18 (18 gauge spall-resistant stainless steel) honeycomb monolith with 200 cells per square inch was washcoated with the co-mingled ceria and alumina. The washcoat loading was 6000 g per cubic foot volume of monolith.

Example Catalyst G was prepared by impregnating the ceria-alumina washcoated metallic monolith with an aqueous solution of Mn(SO$_4$).H$_2$O and Fe$_2$(SO$_4$)$_3$.H$_2$O at a Mn loading of 74 g per cubic foot volume of monolith and an Fe loading of 150 g per cubic foot volume of monolith, drying the catalyst at 120° C. for 1 hour and further calcining it at 450° C. for 30 minutes.

Example Catalyst H was prepared by aging Example Catalyst G for 300 hours at 400° C. in a flow of wet (10 volume % H$_2$O) air which was free of SO$_x$.

Example Catalyst I was prepared by aging Example Catalyst H for 250 hours at 400° C. in a flow of exhaust gas generated from the combustion of propane in excess oxygen to which 5 ppm SO$_2$ was added.

Example Catalyst J was prepared by impregnating the ceria-alumina washcoated monolith with an aqueous solution of Mn(SO$_4$).H$_2$O and Ni(SO$_4$).6H$_2$O at a Mn loading of 120 g per cubic foot volume of monolith and an Ni loading of 95 g per cubic foot volume of monolith, drying the catalyst at 120° C. for 1 hour, calcining it at 450° C. for 30 minutes, and further aging it for 250 hours at 400° C. in a flow of exhaust gas generated from the combustion of propane in excess oxygen to which 5 ppm $SO_2$ was added.

The example catalyst samples were tested for SCR activity in the same manner as described in Example 1 and the results of these tests are also included in Table 1. It is evident from the reactor test results that oxysulfur compounds of manganese or nickel or a mixture of manganese and nickel supported on ceria-alumina have higher SCR activities than the same catalysts supported on alumina alone or than the ceria-alumina carrier alone. The example catalysts representing the invention are not deactivated during use in low concentrations (e.g., less than 200 ppm) of sulfur oxides via decomposition of metal sulfates to metal oxides. High SCR activities due to synergism between ceria and nickel (or manganese) sulfate, and long catalyst life time due to thermal stability of nickel (or manganese) sulfate at low concentrations of sulfur oxides make the catalyst formulations of the invention commercially superior to prior art metal sulfate SCR catalyst formulations. Addition of oxysulfur compounds of iron is optional and the effect is beneficial.

As will be evident from Table 1, the catalysts representative of the invention are all much more effective than catalysts composed of nickel sulfate or manganese sulfate on an alumina only carrier. Compare Examples A-J with Comparative Examples B and C. The Comparative Example A based on iron sulfate gave generally equivalent NO reduction when fresh but its activity dropped off substantially when aged (compare Comparative Catalyst A and D). This was in marked contrast to the catalysts of the invention which maintained their activity even on aging.

Various modifications may be made in the invention described herein. Hence the scope of the invention is defined in the following claims wherein:

I claim:

1. A catalyst consisting essentially of nickel or manganese sulfate, or mixtures thereof, carried by a mixture of ceria and alumina on a support, the ceria comprising from 2-60% by weight of said mixture of ceria and alumina and the manganese sulfate, nickel sulfate or mixture thereof comprising from 0.1-25% by weight of metal based on the carrier weight.

2. The catalyst of claim 1 wherein the support is a ceramic or metal support.

3. The catalyst of claim 1 including iron sulfate.

* * * * *

TABLE 1

| Catalyst | Metal Sulfate | Support | Fresh/Aged | Percent NO Reduction (%) at | | |
|---|---|---|---|---|---|---|
| | | | | 350° C. | 400° C. | 450° C. |
| Comparative A | $Fe_2(SO_4)_3$ | $Al_2O_3$ | Fresh | 84 | 94 | 94 |
| Comparative B | $NiSO_4$ | $Al_2O_3$ | Fresh | 6 | 4 | 4 |
| Comparative C | $MnSO_4$ | $Al_2O_3$ | Fresh | 8 | 8 | 12 |
| Comparative D | $Fe_2(SO_4)_3$ | $Al_2O_3$ | Aged | 43 | 55 | 62 |
| Comparative E | None | $CeO_2$—$Al_2O_3$ | Fresh | 59 | 82 | 74 |
| Example A | $NiSO_4$ | $CeO_2$—$Al_2O_3$ | Fresh | 93 | 98 | 93 |
| Example B | $NiSO_4$ | $CeO_2$—$Al_2O_3$ | Aged | 92 | 99 | 99 |
| Example C | $MnSO_4$ | $CeO_2$—$Al_2O_3$ | Fresh | 89 | 92 | 77 |
| Example D | $MnSO_4$ | $CeO_2$—$Al_2O_3$ | Fresh | 87 | 93 | 85 |
| Example E | $MnSO_4$ | $CeO_2$—$Al_2O_3$ | Aged | 85 | 92 | 88 |
| Example F | $MnSO_4$ $Fe_2(SO_4)_3$ | $CeO_2$—$Al_2O_3$ | Fresh | 88 | 94 | 91 |
| Example G | $MnSO_4$ $Fe_2(SO_4)_3$ | $CeO_2$—$Al_2O_3$ | Fresh | 94 | 98 | 98 |
| Example H | $MnSO_4$ $Fe_2(SO_4)_3$ | $CeO_2$—$Al_2O_3$ | Aged | 92 | 98 | 98 |
| Example I | $MnSO_4$ $Fe_2(SO_4)_3$ | $CeO_2$—$Al_2O_3$ | Aged | — | 96 | 96 |
| Example J | $MnSO_4$ $NiSO_4$ | $CeO_2$—$Al_2O_3$ | Aged | — | 91 | 93 |